United States Patent
LaPlante et al.

(10) Patent No.: US 8,133,177 B2
(45) Date of Patent: *Mar. 13, 2012

(54) SYSTEM AND METHOD FOR ASSESSING CAPILLARY VITALITY

(75) Inventors: Paulita LaPlante, Inver Grove Heights, MN (US); Daniel J. Bartnik, Eden Prairie, MN (US); Victor Kimball, St. Louis Park, MN (US)

(73) Assignee: Vasamed, Inc., Eden Prairie, MN (US)

( * ) Notice: Subject to any disclaimer, the term of this patent is extended or adjusted under 35 U.S.C. 154(b) by 1056 days.

This patent is subject to a terminal disclaimer.

(21) Appl. No.: 12/021,938

(22) Filed: Jan. 29, 2008

(65) Prior Publication Data

US 2008/0183059 A1 Jul. 31, 2008

Related U.S. Application Data

(63) Continuation-in-part of application No. 10/668,750, filed on Sep. 23, 2003, and a continuation-in-part of application No. 11/468,203, filed on Aug. 29, 2006, now Pat. No. 7,736,311.

(51) Int. Cl.
*A61B 5/00* (2006.01)
(52) U.S. Cl. .................. 600/363; 600/504; 600/507
(58) Field of Classification Search ............... 600/504, 600/507, 323, 335, 334, 495, 496, 363, 322, 600/453–456, 300, 386, 391–392; 128/635, 128/668

See application file for complete search history.

(56) References Cited

U.S. PATENT DOCUMENTS

| 3,511,227 A | 5/1970 | Johnson |
| 3,905,889 A | 9/1975 | Macur et al. |

(Continued)

FOREIGN PATENT DOCUMENTS

WO WO 94/23645 4/1994

(Continued)

OTHER PUBLICATIONS

Jin et al. (1997), "End-Tidal PCO$_2$ Serves as an Indicator of Cardiac Output During Experimental Septic Shock," *Crit. Care Med.* 25(1):A122 (Abstract).

(Continued)

*Primary Examiner* — Patricia Mallari
*Assistant Examiner* — Michael D'Angelo
(74) *Attorney, Agent, or Firm* — Barbara A. Wrigley; Oppenheimer Wolff & Donnelly, LLP

(57) ABSTRACT

A device for assessing capillary vitality comprises an inflatable cuff, a blood flow sensor and a pressure sensor in communication with the cuff, a pressure instrument in fluid communication with the cuff for inflation and deflation thereof, a microprocessor coupled to the pressure instrument for controlling airflow, at least one metabolic sensor for measuring a metabolic condition, and a computer program executable by the microprocessor. The pressure instrument includes a source of pressurized air and a conduit connecting the source of pressurized air to the cuff. The microprocessor is arranged to receive inputs from the blood flow, pressure and metabolic sensors. When executed by the microprocessor, the computer program causes the microprocessor to initiate an automatic inflation sequence resulting in a no flow condition, initiate an automatic deflation sequence, automatically qualify a perfusion measurement as an SPP value upon one or more conditions being met during the deflation sequence, and initiate the measurement of at least one metabolic factor.

7 Claims, 5 Drawing Sheets

U.S. PATENT DOCUMENTS

| | | | |
|---|---|---|---|
| 4,016,863 A | | 4/1977 | Brantigan |
| 4,109,647 A | | 8/1978 | Stern et al. |
| 4,155,354 A | * | 5/1979 | Rasmussen .................. 600/393 |
| 4,228,805 A | | 10/1980 | Rosen et al. |
| 4,230,122 A | * | 10/1980 | Lubbers et al. ............... 600/357 |
| 4,324,258 A | | 4/1982 | Huebscher et al. |
| 4,381,011 A | | 4/1983 | Somers, III |
| 4,503,859 A | | 3/1985 | Petty |
| 4,535,786 A | | 8/1985 | Kater |
| 4,538,618 A | | 9/1985 | Rosenberg et al. |
| 4,577,109 A | | 3/1986 | Hirschfeld |
| 4,590,948 A | | 5/1986 | Nilsson |
| 4,593,698 A | * | 6/1986 | Athans ......................... 600/386 |
| 4,596,254 A | | 6/1986 | Adrian et al. |
| 4,632,119 A | | 12/1986 | Reichstein |
| 4,643,192 A | | 2/1987 | Fiddian-Green |
| 4,729,384 A | | 3/1988 | Bazenet |
| 4,729,824 A | | 3/1988 | Gilner |
| 4,759,374 A | | 7/1988 | Kierney et al. |
| 4,785,814 A | | 11/1988 | Kane |
| 4,789,453 A | | 12/1988 | Eberhard et al. |
| 4,800,886 A | | 1/1989 | Nestor |
| 4,816,131 A | | 3/1989 | Bomsztyk |
| 4,833,091 A | | 5/1989 | Leader |
| 4,834,101 A | | 5/1989 | Collison |
| 4,842,783 A | | 6/1989 | Blaylock |
| 4,890,619 A | | 1/1990 | Hatschek |
| 4,892,383 A | | 1/1990 | Klainer et al. |
| 4,919,891 A | | 4/1990 | Yafuso et al. |
| 4,945,896 A | | 8/1990 | Gade |
| 4,966,148 A | | 10/1990 | Millar |
| 4,981,470 A | | 1/1991 | Bombeck, IV |
| 5,006,314 A | | 4/1991 | Gourley et al. |
| 5,098,659 A | | 3/1992 | Yim et al. |
| 5,105,812 A | | 4/1992 | Corman |
| 5,117,827 A | | 6/1992 | Stuebe et al. |
| 5,158,083 A | | 10/1992 | Sacristan et al. |
| 5,166,990 A | | 11/1992 | Riccitelli et al. |
| 5,174,290 A | | 12/1992 | Fiddian-Green |
| 5,251,619 A | | 10/1993 | Lee |
| 5,280,548 A | | 1/1994 | Atwater et al. |
| 5,297,556 A | * | 3/1994 | Shankar ........................ 600/481 |
| 5,329,922 A | | 7/1994 | Atlee |
| 5,330,718 A | | 7/1994 | Hui et al. |
| 5,341,803 A | | 8/1994 | Goldberg |
| 5,368,027 A | | 11/1994 | Lubbers et al. |
| 5,408,999 A | | 4/1995 | Singh et al. |
| 5,411,022 A | | 5/1995 | McCue |
| 5,423,320 A | | 6/1995 | Salzman et al. |
| 5,453,248 A | | 9/1995 | Olstein |
| 5,456,251 A | | 10/1995 | Fiddian-Green |
| 5,479,923 A | | 1/1996 | Rantala |
| 5,536,783 A | | 7/1996 | Olstein et al. |
| 5,579,763 A | | 12/1996 | Weil et al. |
| 5,596,988 A | | 1/1997 | Markle et al. |
| 5,607,644 A | | 3/1997 | Olstein et al. |
| 5,620,000 A | | 4/1997 | Zinser et al. |
| 5,631,340 A | | 5/1997 | Olstein |
| 5,672,515 A | | 9/1997 | Furlong |
| 5,714,121 A | | 2/1998 | Alderete et al. |
| 5,743,259 A | | 4/1998 | Kruse |
| 5,778,878 A | | 7/1998 | Kellam |
| 5,788,631 A | | 8/1998 | Fiddian-Green |
| 6,055,447 A | | 4/2000 | Weil et al. |
| 6,178,342 B1 | * | 1/2001 | Borgos et al. ................. 600/322 |
| 6,254,628 B1 | * | 7/2001 | Wallace et al. ............... 623/1.12 |
| 6,258,046 B1 | | 7/2001 | Kimball et al. |
| 6,501,973 B1 | * | 12/2002 | Foley et al. ................... 600/310 |
| 6,930,608 B2 | | 8/2005 | Grajales et al. |
| 7,736,311 B2 | | 6/2010 | Bartnik et al. |
| 2002/0168618 A1 | | 11/2002 | Anderson et al. |
| 2003/0214408 A1 | * | 11/2003 | Grajales et al. ............ 340/573.1 |
| 2004/0127800 A1 | | 7/2004 | Kimball et al. |
| 2005/0079147 A1 | | 4/2005 | Delaey et al. |
| 2006/0052686 A1 | | 3/2006 | Zhang et al. |
| 2006/0064800 A1 | | 3/2006 | Freund |
| 2006/0287603 A1 | | 12/2006 | Bartnik et al. |
| 2007/0016079 A1 | | 1/2007 | Freeman et al. |
| 2007/0038042 A1 | | 2/2007 | Freeman et al. |
| 2007/0173727 A1 | | 7/2007 | Naghavi et al. |
| 2007/0225614 A1 | | 9/2007 | Naghavi et al. |

FOREIGN PATENT DOCUMENTS

| | | |
|---|---|---|
| WO | WO 98/20794 | 5/1998 |
| WO | WO 00/59372 | 10/2000 |
| WO | WO 2005/030038 | 4/2005 |

OTHER PUBLICATIONS

Nakagawa et al. (1997), "Sublingual Capnometry for Quantitation of the Severity of Hemorrhagic Shock," *Shock* 7:14 (Abstract).

Nakagawa et al. (1997), "$ETCO_2$ as Non-Invasive Indicator of Cardiac Output During Hemorrhagic Shock," *Crit. Care Med.* 25(1):A132 (Abstract).

Nakagawa et al. (1997) et al. (1997), "Sublingual Capnography as an Indicator of Perfusion Failure in Human Patients," *Chest* 112:4S (Abstract).

Nakagawa et al. (1998), "Comparison of Sublingual Capnometry with Gastric Capnometry and Lactate as Indicators of the Severity of Hemorrhagic Shock," *Crit. Care Med.* 26(1):A44 (Abstract).

Ogino et al. (1994), "Reflectance Pulse Oximeter Measuring Central Sa02 From Mouth," Proceedings of the Annual International Conference of the IEEE Engineering in Medicine and Biology Society, Baltimore, 2(16):914-915.

Peterson et al. (1984), "Fiber Optic Sensors for Biomedical Applications," *Science* 224(4645):123-127.

Sato et al. (1997), "Esophageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *Appl. Physiol.* 82(2):558-562.

Seitz (1984), "Chemical Sensors Based on Fiber Optics," *Anal. Chem.* 56(1):16A-34A.

Tang et al. (1988), "Myocardial Preservation During Cardiopulmonary Resuscitation," *Curr. Opin. Crit. Care* 4:155-160.

Vurek et al. (1983), "A Fiber Optic $PCO_2$ Sensor," *Annals Biomed. Engineer* 11:499-510.

Weil (1998), "The Assault on the Swan-Ganz Catheter," *Chest* 113:1379-1386 (1998) (Invited Publication).

Xie et al. (1997) "Sublingual Capnometry for Quantitation of the Severity of Septic Shock," *Shock* 7:13-14 (Abstract).

Vlad-Adrian Alexandrescu, M.D., et al., Selective Primary Angioplasty Following an Angiosome Model of Reperfusion in the Treatment of Wagner 1-4 Diabetic Foot Lesions; Practice in a Multidisciplinary Diabetic Limb Service, J. Endovasc Ther, 2008, pp. 580-593, vol. 15, International Society of Endovascular Specialists, Belgium.

Richard F. Neville, et al., Revascularization of a Specific Angiosome for Limb Salvage: Does the Target Artery Matter?, Annals of Vascular Surgery, 2008, pp. 1-7, Elsevier, USA.

Xie et al. (1997) "Sublingual Capnometry for Quantitation of the Severity of Septic Shock," *Shock* 7:13-14 (Abstract).

Benazzo et al., "Endothelin-Induced Vasoconstriction in Rabbit Nasal Mucosa," *Acta Otolaryngol* (Stockh), vol. 114(5), pp. 544-546 (1994).

Bertuglia et al., "Venular Oscillatory Flow During Hemorrhagic Shock and No Inhibition in Hamster Cheek Pouch Microcirculation," *Microvascular Research*, vol. 54, pp. 23-242 (1997).

Casasco et al., "Occurrence, Distribution and Possible Role of the Regulatory Peptide Endothelin in the Nasal Mucosa," *Cell & Tissue Research*, vol. 274(2), pp. 241-247 (1993).

Friberg et al., "Habitual Snorers and Sleep Apnoics Have Abnormal Vascular Reactions of the Soft Palatal Mucosa on Afferent Nerve Stimulation," *The Laryngoscope*, vol. 108(3), pp. 431-436 (1998).

Grudemo et al., "Rhinostereometry and Laser Doppler Flowmetry in Human Nasal Mucosa: Changes in Congestion and Microcirculation During Intranasal Histamine Challenge," *ORL*, vol. 59, pp. 50-56 (1997).

Grudemo et al., "Studies of Spontaneous Fluctuations in Congestion and Nasal Mucosal Microcirculation and the Effects of Oxymetazoline Using Rhinostereometry and Micromanipulator Guided Laser Doppler Flowmetry," *American Journal of Rhinology*, vol. 13(1), pp. 1-6 (1999).

Hoke et al., "Blood-Flow Mapping of Oral Tissues by Laser Doppler Flowmetry," *International Journal of Oral & Maxillofacial Surgery*, vol. 23(5), pp. 312-315 (1994).

Jin et al., "Decreases in Organ Blood Flows Associated with Increase in Sublingual $PCO_2$ During Hemorrhagic Shock," *J. Applied Physiol.*, vol. 85(6), pp. 2360-2364 (1998).

Kelley et al., "Comparison Between the Uptake of Nitrous Oxide and Nitric Oxide in the Human Nose," *Journal of Applied Physiology*, vol. 85(4), pp. 1203-1209 (1998).

Klinger et al., "Untersuchungen zur Mikro-zirkulation der Nasenschleimhaut bei Verwendung von Ballon-tamponaden," ("The Influence of Cuffed Epistaxis Catheters on Nasal Mucosa Blood Flow Measured by Laser Doppler Flowmety") *Laryngo-Rhino-Otologie*, vol. 76, pp. 127-130 (1997).

Lacroix et al., "Sympathetic Vascular Control of the Pig Nasal Mucosa (III): Co-Release of Noradrenaline and Neuropeptide Y," *Acta Physiologica Scandinavica*, vol. 135(1), pp. 17-28 (1989).

Marais et al., "A Preliminary Comparison of the Effects of Halothane and Isoflurane on Nasal Mucosal Blood Flow," *Rhinology*, vol. 31(1), pp. 31-83 (1993).

Weaver et al., "Effect of Internal Maxillary Arterial Occlusion on Nasal Blood Flow in Swine," *The Laryngoscope*, vol. 109(1), pp. 8-14 (1999).

Ylipaavalniemi et al., "Effect of Local Anaesthesia on the Blood Perfusion of Oral Mucosa Measured by the Laser Doppler Method," *Proceedings of the Finnish Dental Society*, vol. 79(2), pp. 58-61 (1983).

D. Mukherjee, et al., Development of a Multicenter Peripheral Arterial Interventional Database: the PVD-Q12. Am. Heart J., 149, (2005), pp. 1003-1008.

US 5,596,688, 01/1997, Markle et al. (withdrawn)

* cited by examiner

SYSTEM AND METHOD FOR ASSESSING CAPILLARY VITALITY

CROSS REFERENCE TO RELATED APPLICATIONS

This application is a continuation-in-part of application Ser. No. 10/668,750 filed Sep. 23, 2003 and a continuation-in-part of application Ser. No. 11/468,203 filed Aug. 29, 2006, the entireties of which are hereby incorporated by reference.

BACKGROUND OF THE INVENTION

1. Field of the Invention

The present invention relates to a system and method for assessing capillary vitality. In particular, the present invention relates to an instrument for the automated measurements of skin perfusion pressure and tissue gases in a local or regional body site to allow a clinician to predict the ability of a wound to heal. The tissue gases principally include $CO_2$, but numerous other gases may also be measured.

2. Description of the Related Art

Transcutaneous oximetry (TCOM) is a commonly used tool for vascular assessment. TCOM is uniformly used to assess the severity of arterial blockage; assess the potential for healing of wounds, ulcers and amputations; evaluate the outcome of a revascularization procedure; and assess the severity and progression of peripheral vascular disease. TCOM measurements are conducted in a variety of ways. One measurement device uses a polarographic sensor, a silver anode, an electrolyte, an oxygen permeable membrane and a heating section to control temperature. When the sensor, placed near the measurement site, detects oxygen, it causes an electrochemical reaction that results in an electrical current to flow through the cathode. An amplifier connected to the cathode measures the amount of current and correlates it to the amount of oxygen reaching the skin. This information is displays as $TcPO_2$. The clinician uses the $TcPO_2$ value to assess the ability of the wound, ulcer, or amputation to heal, the success of revascularization, and otherwise predict the behavior of healing. However, problems abound using this conventional device as the standard predictor for wound healing. This is because while oxygen can be present at the measurement site, the presence of oxygen is not necessarily a predictor of a tissue's ability to heal. Thus a very low $TcPO_2$ level is thought to be predictive of a wound not having the ability to heal. However, a clinician evaluating a high or normal $TcPO_2$ would conclude that the wound does have the ability to heal when that is not necessarily the case. This is especially true with respect to lower extremity ulcers. (See Faglia et al Angiographic Evaluation of PAOD and its Role as a Prognostic Determinant for Major Amputation in Diabetic Subjects with Foot Ulcers. Diabetic Care 1998; 21:4; 625.)

Pulse oximeters are another device that monitor the oxygenation in a patient's arterial blood. Conventional pulse oximeters measure the ratio of changing absorbance of red and infrared light caused by the difference in color between oxygen-bound (bright red) and oxygen unbound (dark red or blue, in severe cases) blood hemoglobin at the measuring site. However, oxygen may reach the measurement site either as it is presently being bound to hemoglobin or unbound from hemoglobin thus skewing the predictive value. Falsely high or low readings will occur when hemoglobin is bound to something other than oxygen such as carbon monoxide. Also, the conventional pulse oximeter is dependant on pulsatile flow so where flow is sluggish, as is frequently the case with wounds and ulcers, the pulse oximeter is less able to provide accurate readings. Pulse oximeters measure only oxygenation; they do not measure carbon dioxide levels, blood pH or sodium bicarbonate levels. Further, although pulse oximetry is used to monitor oxygenation, it cannot determine the metabolism of oxygen and other gases being used by the patient. For this purpose, tissue carbon dioxide levels must be measured. It is also known that oximetry is not a complete measure of circulatory sufficiency. As pointed out above, if there is insufficient blood flow or insufficient hemoglobin in the blood, such as patients with anemia, tissues can suffer hypoxia despite high oxygen saturation in the blood that does arrive to the wound site.

Other measurement devices such as hyperspectral imaging which tracks chromophores and thermal imaging which detects heat secondary to blood flow, do not assess the ability of a capillary bed to overcome resistance, a mechanical factor. Hyperspectral imaging is built on the concept that tissues have optical signatures or chromophores that reflect their chemical characteristics. The two major chromophores of physiological relevance in hyperspectral imaging are oxyhemoglobin (OxyHb) and deoxyhemoglobin (DeoxyHb). When measured by hyperspectral imaging, these chromophores delineate local oxygen delivery and extraction within the tissue microvasculature. However, detecting the presence or absence of oxygen does not take into account the functional assessment of the capillary bed, which can only be done by creating a challenge environment in which capillary flow is monitored during the application of occlusive pressure and controlled release of that pressure. This type of measurement is termed "Skin Perfusion Pressure" (SPP). These measurements are informative to the physician because fluid movement in the capillaries is possible in low flow states but the opening pressure required by the capillaries to overcome occlusion may not be sufficiently adequate to maintain tissue health.

In damaged tissues there is a marked difference in capillary performance. For example, the capillary density of the skin of the foot is significantly reduced in patients with arterial ulceration compared with that in patients with claudication and healthy subjects. (See e.g. Lamah, Mortimer, Dormandy. Qualitative study of capillary density in the skin of the foot in peripheral vascular disease. British Journal of Surgery 86(3): 342-348, 1999.) How this process evolves is likely more a function of damage that is manifest earlier in the release of downstream mediators and mechanisms that result in irreversible tissue injury.

The assessment of tissue carbon dioxide concentration has also been useful in perfusion assessment. See e.g. Fries et al. "Increases in tissue $PCO_2$ during circulatory shock reflect selective decreases in capillary blood flow," Crit. Care Med. 2006; 34:446-452. At predictable tissue $CO_2$ levels and durations, tissue damage is compromised. Carbon dioxide production, which is associated with metabolism, continues in tissues even during conditions of low blood flow. The concentration of carbon dioxide increases in tissues experiencing low blood flow because the carbon dioxide is not rapidly carried away. This carbon dioxide increase (measured as an increase in partial pressure of $CO_2$ ($PCO_2$) in turn results in a decrease in pH in nearby tissue. Therefore, the ability of a tissue to heal may be assessed by measuring pH or $PCO_2$ at these sites.

Significantly, one may have blood flow at a site (and conventional methods will detect a near normal to normal reading of $O_2$) but accumulated $CO_2$ is not cleared secondary to ongoing production of $CO_2$ such as that attributed to necrotic tissues. Therefore, a physician assessing tissue viability may draw an erroneous conclusion thereby compromising patient health. Notably, when limb hypoxia is due to ischemia (low blood flow) PCO2 levels significantly increase. When limb hypoxia is due to hypoxemia (maintained blood flow) PCO2 levels remain constant. However, when blood flow is maintained and a normal oxygen supply is available but PCO2 levels remain constant, then other sources of carbon dioxide production are suspected. Viewed another way, increased tissue carbon dioxide is always associated with compromised tissue health. This is very well illustrated by the significant increases in PCO2 levels accompanied by decreased tissue blood flow seen in septic states. These considerations argue for assessing both mechanical and metabolic factors to accurately assess capillary vitality in low and high blood flow situations.

Thus, a system is needed that overcomes the problems associated with using conventional measurements such as TCOM, the measurement of bound or unbound hemoglobin, thermal imaging and/or hyperspectral imaging to assess wound healing potential. A system is needed that can accurately assess wound healing potential in cases where blood flow is sluggish and in cases where blood flow is high; and one that does not rely solely on oxygen measurements as the predictor of a tissue's ability to heal. Such a system would be a marked improvement over conventional systems and would allow physicians to assess wound healing potential, monitor pre- and post-surgical therapy, assist in arterial reconstruction planning and post-procedure monitoring, amputation planning and post-procedure monitoring; and assist in the diagnosis of peripheral arterial disease, critical limb ischemia and other microcirculatory derangements.

BRIEF SUMMARY OF THE INVENTION

Accordingly it is an object of the present invention to overcome the problems and disadvantages of relying on TCOM measurements, measurements of bound and unbound hemoglobin, and/or hyperspectral imaging to assess wound healing.

It is a further object of the present invention to overcome the problems and disadvantages of relying solely on the measurement of tissue gases such as oxygen to assess capillary vitality.

It is an object of the present invention to provide a system that assesses capillary vitality, in other words the capillary bed's ability to overcome resistance, in high blood flow and low blood flow states.

It is also an object of the present invention to combine mechanical measurements such as blood flow with metabolic measurements such as measurement of tissue gases into one system that can accurately and reliably predict a tissue's ability to heal.

It is also an object of the present invention to automate the method and system of assessing capillary vitality to ensure reproducible results and clear comparisons of results over time. Such a system would be less traumatic to the patient, would reduce the amount of time necessary to take the measurements, be more cost effective, and enable the clinician to instantly visualize the relationship between capillary flow and metabolism.

The present invention provides a more effective method of assessing capillary vitality and the degree of perfusion failure by coupling two diagnostic modalities (skin perfusion pressure and tissue CO2) as part of one system that can address the conventional problems of reproducibility and that automatically determines tissue carbon dioxide and skin perfusion pressure.

These and other objects and advantages of the present invention will become apparent during the course of the following detailed description and appended claims.

The invention may best be understood with reference to the accompanying drawings, wherein an illustrative embodiment is shown.

DETAILED DESCRIPTION OF THE INVENTION

Figure 1:
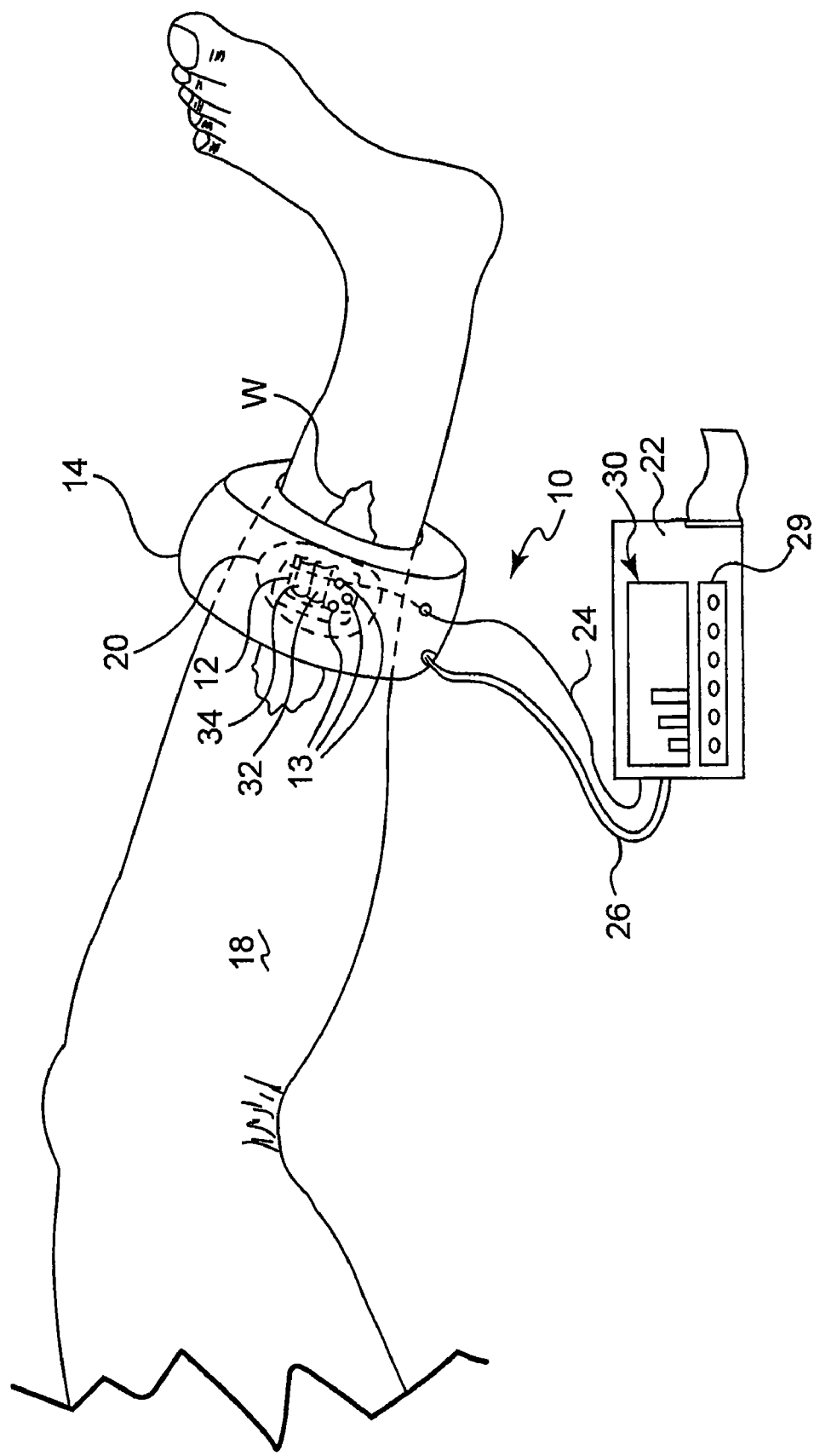
FIG. 1 is a schematic representation of an embodiment of the measurement device in use with a patient in accordance with the present invention in which the cuff and applicable tissue gas sensors are placed in the wound.

The present invention is based on the inventors' discovery that the measurement of metabolic factors such as the presence or absence of tissue gases alone, for example oxygen and carbon dioxide, or the measurement of mechanical factors alone, such as blood flow, is not necessarily indicative of capillary vitality in both high and low blood flow states at local and/or regional tissue sites. Rather, the inventors' have found that the ability of capillaries to open and allow the transport of gases in the presence of challenge is a superior indicator of wound healing potential. Thus, the present invention is directed to the measurement of both mechanical and metabolic factors to assess and monitor capillary vitality. This combination of measurements as a predictor of capillary vitality yields more than just predictable results to a physician.

Capillary vitality is defined as the sum of capillary opening pressure (a mechanical parameter) and the metabolism of gases in native capillary flow (a metabolic parameter). In other words, capillary vitality is the ability of the capillaries to function in the presence of a challenge, i.e. not only will the capillary open but it will allow the transport of gases such as CO2 and O2.

Challenge as used herein means metabolic challenges and/or mechanical challenges.

A non-limiting list of mechanical challenges includes controlled occlusion of blood flow, heat, exercise as a stressor, external pressure applied via cuffs, acoustical challenges such as ultrasound, applied electrical fields, and the like.

A non-limiting list of metabolic challenges include exposure of the tissue site to gases and introduction of pharmacologic agents.

Both the measurement of mechanical and metabolic factors are critical to the proper assessment of the ability of tissue to heal. The ability of tissue to heal informs the physician in cases of severe burns, wounds, ulcers, site for amputation and subsequent amputation, revascularization, surgical anastomosis, and a variety of other patient conditions.

Mechanical Parameters. The methods and devices of the invention measure blood flow in tissue at a convenient local site such as in the wound or peri-wound and are thus performed in a minimally invasive manner. In situations where the ulcer or wound is severe peri-wound measurements may be utilized effectively. In general, these measurements are made by placing a blood-flow sensor such as a laser-Doppler sensor or an ultrasound Doppler sensor locally in the wound or adjacent the wound site and using the sensor to measure blood flow at the selected site. Alternatively, continuous monitoring measurements can be utilized.

Skin perfusion pressure measurements are taken to determine whether local blood flow, i.e. capillary perfusion, of a local or regional body site having an ulcer or wound is sufficient to support wound healing. The accurate measurement of this parameter, therefore, is critical to physicians who treat patients suffering from open surface wounds resulting from complications from diabetes, pressure ulcers, burns, accidents, and the like.

Skin or surface perfusion pressure may be measured utilizing a device coupled to a laser Doppler or other type of optical sensor. For example, U.S. Pat. No. 6,178,342 to Borgos et al. discloses a surface perfusion pressure instrumentation used in conjunction with a laser Doppler probe that measures the "amount" of moving blood contained within a microvascular observation volume in percent tissue hematocrit. This measurement is taken as a function of applied pressure. The laser Doppler optical probe defines an observation volume in the skin near the surface of the patient and a pressure cuff is used to manually apply pressure to the limb near the optical probe.

The laser Doppler sensor is placed against the skin under a pneumatic cuff that is secured to the affected limb, i.e. toe, ankle, arm, leg, etc. A user using an inflation bulb manually inflates the pneumatic cuff. The inflation pressure must be sufficiently high to stop local blood flow at the site of the optical probe. A display instrument is coupled to the optical probe typically via a fiber optic cable, and to the inflation bulb through a tube. Deflation starts and the optical probe monitors the number of moving red blood cells moving into or out of the observation volume without regard to velocity. The number of moving red blood cells detected within the control volume is expressed as a percent and displayed on the display monitor. This value is shown as both a numeric value and a bar graph on the Y-axis. The instrument also measures the pressure within the cuff and displays the applied cuff pressure in millimeters of mercury on the X-axis of the display. A moving bar chart along the X-axis shows the operator which cuff pressure is currently being measured. As pressure is slowly manually released, an indicator of blood flow return is provided in bar chart form.

The optical probe monitors microcirculatory flow within the observation volume of tissue. Microcirculation detected within the observation volume of tissue is expressed as a percent and displayed on the Y-axis of the perfusion pressure display instrument. The percent value is shown as both a numeric value, typically from 0% to 10% and graphically is shown as a bar graph on the Y-axis of the instrument display 30. The device also measures the pressure within the cuff and displays the applied cuff pressure in millimeters of mercury on the X-axis of the display in descending uniform increments. A graphical line moves along the X-axis and shows the operator the cuff pressure that is currently being measured.

The optical probe includes at least a laser transmitter fiber and at least one receiver photodiode. In an alternative embodiment, the laser or photodiode, or both, may be placed in the optical probe without a need for fiber optic elements. In operation, coherent light supplied from a solid state, or other laser device within the perfusion pressure display instrument is conducted to the transmitter fiber that is in contact with the patient's wound through the pressure cuff bladder. Photons emitted from the transmit fiber are scattered by the patient's tissues. A small portion (less than 5%) of the emitted photons is collected by the receiver fiber. The spacing between the fibers and the optical apertures of the fibers establish the volume of tissue that is monitored. Typically a single transmitter fiber is used with a pair of receiver fibers. The nominal fiber core diameter is on the order of 50 to 100 microns and is used to establish an observation volume of approximately one to two cubic millimeters. A suitable optical probe is disclosed in U.S. Pat. No. 5,654,539 to Borgos, as discussed above.

Those skilled in the art will recognize that there are many ways to determine the point at which microcirculatory flow returns to a given observation volume. For example, visual observation such as the change in color of the observation site; ultra-sound; optical plethysmography, measurements of increases in temperature; sound, e.g. a microphone for pulsatile flow in the macrocirculation; metabolic indicators such as $PCO2$ or lactate; and bioimpedance or pulse oximetry or both, each with a pulsatile measurement and a blood volume measurement.

Some back-scattered photons are frequency shifted by moving cells present in the microcirculation. The collected photons are collected by the capillary vitality instrument via a cable where they impinge on a photodiode. Thus, photons are impinging on the photodiode as a result of scattering off moving and stationary cells. The photodiode voltage contains both frequency and power information. The Doppler shifted frequency is related to cell velocity while the spectral power information is related to the volume of moving cells at that given frequency. The DC signal component results from the total number of photons received by the receive fiber. The AC signal component results from the mixing of frequency shifted photons with photons from stationary structures. If the number of moving cells present within the observation volume increases then the magnitude of the AC component will increase while the DC offset will remain nearly constant. The AC component increases because more returned photons undergo a Doppler shift. The DC component remains nearly constant because the total number of photons scattered by collisions with stationary cells within the measurement volume is reduced only slightly by moving cells. Therefore, the perfusion measurement is proportional to the ratio of the AC signal to the DC signal, which is an indication of the volume of moving cells in the observation volume of tissue. This type of measurement is commonly computed with both analog and digital signal processing. For example, it is common to convert the AC signal to an RMS equivalent through analog processing. It is these values that are presented to the A/D converter. The microprocessor then may square these digitized values prior to forming the ratio. The ratio value may be scaled by an empirically derived scaling factor that depends on the gain distribution throughout the signal processing paths.

Other methods and techniques for using laser-Doppler techniques and devices to measure blood flow are known in the art, and may be found in such references as, e.g., U.S. Pat. No. 3,511,227 to Johnson, U.S. Pat. No. 4,596,254 to Adrian et al., and U.S. Pat. No. 4,590,948 to Nilsson. Methods and techniques for using ultrasound-Doppler techniques and devices to measure blood flow are known in the art, and may be found in such references as U.S. Pat. No. 4,324,258 to Huebscher et al. and U.S. Pat. No. 4,759,374 to Kierney et al.

The inventors of the present invention have also discovered that the measurement of skin perfusion pressure can be further refined by measuring optical plethysmography. A photoplethysmograph for measuring optical plethysmography uses light absorbance technology to reproduce waveforms produced by pulsating blood. Typically non-visible infrared light is emitted into the skin. More or less light is absorbed, depending on the blood volume in the skin. The backscattered light corresponds with the variation in blood volume. Blood volume changes are then determined by measuring the reflected light and using the optical properties of tissue and blood. The optical plethysmography measurement may be obtained by volume displacement plethysmography or by electrical impedance plethysmography as those skilled in the art can appreciate. Typically the tissue under investigation is bathed with light of a suitable wavelength and the resultant scattered light is measured with a silicon photodiode. The received signal is assumed to be a measure of volume changes due to localized blood flow. Optical plethysmography measurements may be used in conjunction with the skin perfusion pressure measurements in accordance with the present invention.

Thus, laser-Doppler, ultrasound-Doppler, and other blood-flow measurement devices such as devices to measure skin perfusion pressure and optical plethysmography can be used to provide direct measures of blood flow in tissues. The present invention provides novel methods using such measurements to detect and quantify blood flow in tissues susceptible to low blood flow effective to detect capillary vitality in a local or regional wound site in a patient and thus the ability of the wound or tissue to heal. These measurements may be used in conjunction with each other and additionally in conjunction with measurements of pH, $PCO_2$, and $Sa\,O_2$ as described hereinafter.

Preferably, the blood flow sensor in accordance with the present invention may be positioned in the wound or peri-wound, preferably with the sensor lying immediately above or at the surface of the wound. To minimize patient discomfort, a patch may be placed over the wound with the blood flow sensor placed in or on top of the patch. Alternatively the patch may be a sterile, single use cover that is integrated into the system in accordance with the present invention. If the patch is used in conjunction with the measurement of metabolic parameters as hereinafter described, the patch must be permeable in order to accurately measure tissue gases. The blood flow sensor may also be placed adjacent the surface of the wound that will otherwise minimize discomfort to the patient.

The blood-flow sensor lies in the wound or adjacent the surface peri-wound, in order that it effectively measures blood flow in the tissue. Placement of a blood-flow sensor adjacent the tissue's surface provides a very good quantification of local and/or regional perfusion at all times.

The blood-flow sensor used in the methods and devices of the invention may be any single or arrayed blood-flow sensor suitable for detection of blood flow in the manner described herein, such as laser-Doppler blood-flow sensors, ultrasound-Doppler blood-flow sensors, imaging sensors and so forth. For example, the preferred blood-flow sensor is a laser-Doppler blood-flow sensor.

An exemplary blood-flow sensor of this type is manufactured by Vasomedics (2963. Yorkton Blvd., St. Paul, Minn. 55117-1064; (800) 695-2737)). For example, the Laserflo BPM.sup.2 may be used to provide continuous tissue perfusion data which can be used to practice the present invention.

The blood flow measurement taken with the blood-flow sensor placed against the tissue's surface may be used in conjunction with the SPP index and/or the optical plethysmography index. In order to assess perfusion failure in a patient with this embodiment, one first determines the expected range of measurements for subjects of similar age and health status as the patient as normal measurements of skin perfusion pressure and optical plethysmography may vary with the age of the subject. For a healthy patient, these two indices will be close to one. The blood flow in the wound of the patient, or peri-wound, is determined. Next, the skin perfusion pressure and/or the optical plethysmography measurement is taken. Each of these values are compared with the expected value for a normal subject. In addition, the rate-of-change of the patient's blood flow is measured over time with these measurements. Rising values of blood flow, and an SPP index and an optical plethysmography index close to one may tend to indicate recovery but the measurement of $PCO_2$ and other metabolic factors in conjunction with these measurements is critical to an accurate assessment of local perfusion and capillary vitality.

In addition, as there are many co-morbid factors, e.g. diabetes, that may affect an accurate measurement of blood flow, the use of blood flow measurements in conjunction with the SPP index and the optical plethysmography index allows the physician to more accurately monitor capillary vitality and recovery. These measurements may also be used in conjunction with each other and additionally in conjunction with measurements of pH, $PCO_2$, and $Sa\,O_2$ as hereinafter described.

Metabolic Parameters. In addition to skin perfusion pressure, as described above, to accurately assess capillary vitality in accordance with the present invention, $PCO_2$, $O_2$, NADH, and/or pH may be measured in a patient at a local site in the wound itself or at a regional site, such as peri-wound. These measurements are taken in conjunction with, at the same time or shortly before or shortly after the mechanical measurements described above, such as continuous perfusion monitoring blood flow, to provide information useful for assessing capillary vitality in a patient.

For example, $PCO_2$ may be measured using a $CO_2$ sensor such as a pH-sensing $PCO_2$ sensor. Such $PCO_2$ sensors may have, for example, a membrane that is permeable to $CO_2$, and that separates a sodium bicarbonate or carbonic acid ($HCO_3$) solution from the environment. A pH sensor in the device measures the pH of the sodium bicarbonate solution. Two exemplary $CO_2$ sensors of this type are manufactured by Microelectrode, Inc. and Nihon Kohden (ISFET $PCO_2$ sensor).

Alternatively, the $CO_2$ sensor may comprise an optical $PCO_2$ sensor. Structures, properties, functions, and operational details of fiber optic chemical sensors can be found in U.S. Pat. Nos. 4,577,109; 4,785,814; and 4,842,783, as well as in Seitz, "Chemical Sensors Based on Fiber Optics," Anal. Chem. 56(1):16A-34A (1984). Fiber optic sensors for monitoring $CO_2$ that may be suitable for use in the present invention include, but are not limited to, those described in U.S. Pat. Nos. 4,800,886; 4,892,383; 4,919,891; 5,006,314; 5,098, 659; 5,280,548; and 5,330,718. Other exemplary fiber optic CO2 sensors are described in Peterson et al. "Fiber Optic Sensors for Biomedical Applications," Science 224(4645): 123-127 (1984) and Vurek et al. "A Fiber Optic $PCO_2$ Sensor," Annals Biomed. Engineer. 11:499-510 (1983).

A suitable optical CO2 sensor is described in U.S. Pat. No. 5,714,121 ('121) to Alderete et al., which pertains to an optical CO2 sensor and method of manufacture thereof; a preferred sensor system and method of using the aforementioned optical CO2 sensor is described in U.S. Pat. No. 5,672,515 ('515) to Furlong. In general, the sensor of the '121 patent is composed of a single optical fiber having a distal tip and a proximal region for communication with a means for receiving a signal from the distal tip. Light of a predetermined wavelength is directed through the optical fiber towards the distal tip, and emitted fluorescent light returns along the fiber to be detected and converted to a CO2 concentration value. A capsule, composed of a CO2-permeable silicone material, is arranged over the distal tip at a predetermined position. The capsule contains an indicator solution having a suitable pH-sensitive indicator component, generally a fluorescent dye, and substantially no air. Examples of fluorescent dyes include without limitation fluorescein, carboxyfluorescein, seminaphthorhodafluor, seminaphthofluorescein, naphthofluorescein, 8-hydroxypyrene 1,3,6-trisulfonic acid, trisodium salt ("HPTS") and dichlorofluorescein, with HPTS particularly preferred. A sealing means provides a liquid-tight seal and affixes the capsule onto the distal tip.

Optical CO2 sensors are generally used by contacting the distal end of the sensor with the tissue site or can be used in a peri-wound location. Light of a predetermined wavelength is directed from an external source, through the optical fiber, impinging distally on the encapsulated indicator composition. The intensity of the emitted fluorescent light returning along the fiber is directly related to the concentration of CO2 in the sample, as a result of the pH-sensitive indicator material present at the fiber tip (i.e., the pH of the indicator solution is directly related to CO2 concentration, as a result of carbonic acid formation). The emitted light is carried by the optical fiber to a device where it is detected and converted electronically to a CO2 concentration value. The sensor may additionally have a reference dye present in the indicator composition. The intensity of the light emitted from the reference dye may be used to compensate, via ratioing, the signal obtained from the indicator. A more preferred system for determining PCO2 is described in the '515 patent, directed to a simultaneous dual excitation/single emission fluorescent sensing method, wherein light of two different wavelengths is used to excite a single fluorescent indicator species, with one of the two wavelengths at the isosbestic point. The two fluorescence emission signals that result are ratioed to provide the desired measurement.

Suitable pH sensors include optical pH sensors as described in U.S. Pat. Nos. 5,536,783 and 5,607,644 to Olstein et al. Such optical sensors include a chemical pH sensor means, capable of responding to changes in pH in nearby tissues and fluids, which is incorporated into a fiber optic waveguide assembly so as to interact with the tissue environment into which the pH sensor means is placed. The sensor may be placed may be placed in the wound, ulcer, or other site such as the site of revascularization, or adjacent the wound, ulcer or other measurement site in a patient's body. Typically, the responses of the chemical sensor cause changes in the optical properties of the chemical sensor/optical waveguide assembly, so that pH changes near the tip of the assembly may be monitored and assessed by the user at another portion of the apparatus, e.g., at a portion of the apparatus remaining external to the patient's body. For example, as described in the aforementioned U.S. patents, the pH sensor means may comprise a fluorescent poly(urethrane) copolymer that fluoresces in response to irradiation, wherein the fluorescence is dependent on the pH of the environment being monitored.

Similarly, SaO2 sensors can be used to measure oxygen saturation at the tissue site. oxygen saturation (SaO2) measures the percentage of hemoglobin binding sites in the bloodstream occupied by oxygen. At low partial pressures of oxygen, most hemoglobin is deoxygenated. At around 90% (the value varies according to the clinical context) oxygen saturation increases according to an oxygen-hemoglobin dissociation curve and approaches 100% at partial oxygen pressures of >10 kPa.

Venous oxygen saturation (SVO2) may also be measured locally in accordance with the present invention to determine how much oxygen the wound consumes. Under clinical treatment, an SVO2 below 60%, indicates that the wound site is in lack of oxygen, and ischemic diseases occur.

In certain cases and situations a permeable patch may be utilized in conjunction with the sensor for measuring tissues gases. The permeable patch may be placed over the wound, ulcer or other site to protect the wound during the measurement process.

The sensors of the present invention used to measure metabolic parameters are incorporated into a capillary vitality measurement system as described herein.

Operation. Thus, the invention provides a method and device for assessing capillary vitality and the ability of a tissue to heal, which methods may be performed manually and rapidly, with little equipment set-up required, and with minimal or substantially no invasion, and thus minimal risk of harm to the patient and an improved probability of patient compliance.

Alternatively, co-pending application Ser. No. 11/468,203 discloses a system and automated method for measuring skin perfusion pressure which also adjusts for motion artifact. This system may be adapted for use with the present invention. Referring to FIG. 1, a schematic diagram depicting a representative, but not limiting, capillary vitality monitoring system 10 is illustrated. The capillary vitality monitoring system 10 broadly includes optical blood flow probe or sensor 12; PCO2, pH, NADH, SaO2 and other metabolic sensors 13; pressure cuff 14, optional permeable patch 15; and pressure instrument 22, and display monitor 30. When optional permeable patch 15 is used, optical blood flow probe 12 may be positioned underneath pressure cuff 14 and on top of permeable patch 15 to avoid direct contact of optical blood flow probe 12 with wound W on patient's limb 18. Alternatively, optical blood flow probe 12 may be positioned distal to cuff 14 or inside cuff bladder 14. In an alternative embodiment, cuff 14 may include a transparent window to observe optical blood flow probe 12. PCO2, pH, NADH, SaO2 sensors 13 may also be integrated into the cuff 14. In such a case cuff 14 may be made of a gas permeable material. The skin perfusion pressure instrument inflates the pressure cuff 14 through tube 26. The size of pressure cuff 14 may be varied depending on whether the limb involved is the arm, toe, leg, ankle, etc. but must be capable of sustaining a sufficiently high pressure (above systolic) to stop local or regional (in the case where measurements are taken peri-wound) capillary blood flow at the site of the optical probe 12 in the observation volume of tissue 20. The observation volume of tissue 20 may be at the same location as the applied pressure, at a location near the applied pressure, or distal from the applied pressure, e.g. where flow is measured on the toe and pressure is applied at the ankle. The skin perfusion instrument 22 is coupled to the optical probe 12 via a fiber optic cable 24, and the pressure cuff 14.

Optical probe 12 depicted in FIG. 1 includes at least a laser transmitter fiber 32 and at least one receiver photodiode 34. In an alternative embodiment, the laser or photodiode, or both, may be placed in probe 12 without a need for fiber optic elements. In operation, coherent light supplied from a solid state, or other laser device within the perfusion pressure display instrument 22 is conducted to the transmitter fiber 32 that is in contact with the patient's skin through the pressure cuff 14 bladder. Photons emitted from the transmitter fiber 32 are scattered by the patient's tissues. A small portion (less than 5%) of the emitted photons is collected by the receiver fiber 34. The spacing between the fibers and the optical apertures of the fibers establish the volume of tissue that is monitored. Typically a single transmitter fiber is used with a pair of receiver fibers. The nominal fiber core diameter is on the order of 50 to 100 microns and is used to establish an observation volume of approximately one to two cubic millimeters. A suitable optical probe is disclosed in U.S. Pat. No. 5,654,539 to Borgos, the entirety of which is hereby incorporated by reference.

Figure 2:
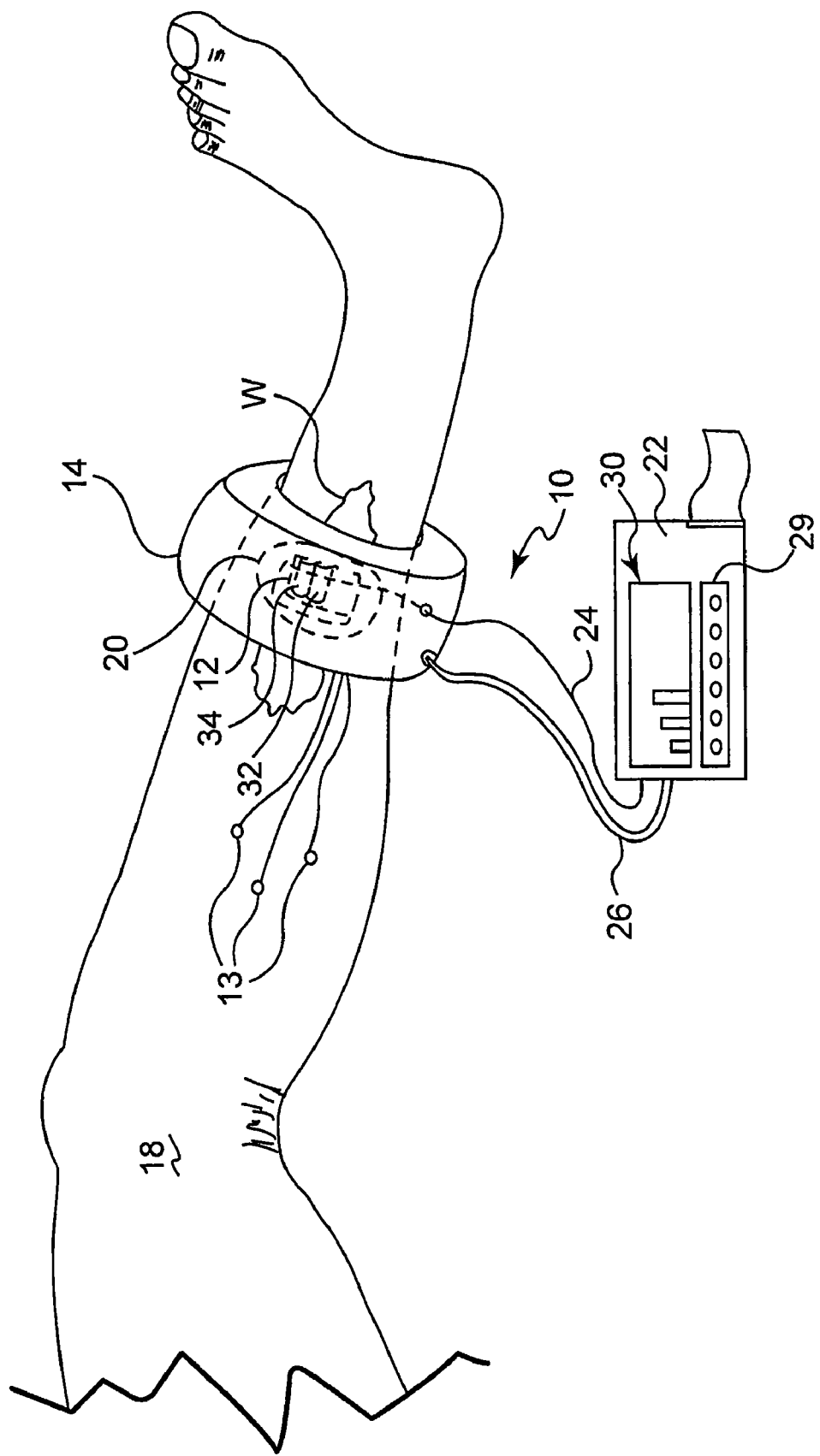
FIG. 2 is a schematic representation of an embodiment of the measurement device in use with a patient in accordance with the present invention in which the cuff is placed in the wound and the applicable tissue gas sensors are placed peri-wound.
Figure 3:
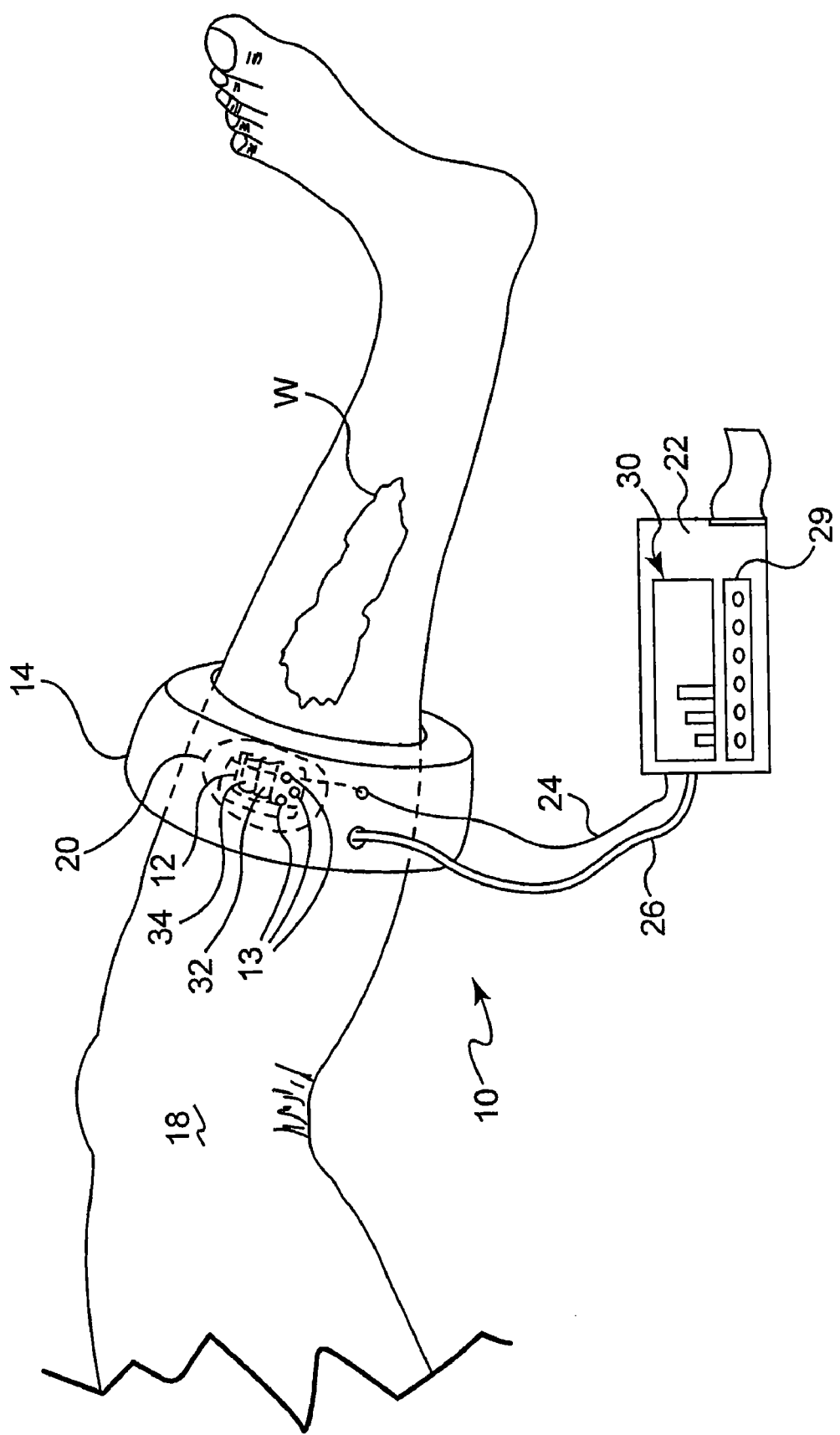
FIG. 3 is a schematic representation of an embodiment of the measurement device in use with a patient in accordance with the present invention in which both the cuff and the applicable tissue gas sensors are placed peri-wound.

Measurements of PCO2, pH, NADH, SaO2 and other tissue gases are also taken in conjunction with the skin perfusion measurement. Measurement of metabolic factors may be taken in the wound when for example the sensors are integrated into the pressure cuff, as illustrated in FIG. 1. Alternatively, and in accordance with physician preference, the metabolic measurement sensors 13 may be utilized peri-wound while the blood flow and pressure sensors are placed in the wound W as illustrated in FIG. 2. Furthermore, measurements using blood flow and pressure sensors may also be taken peri-wound in conjunction with measurements taken by the metabolic sensors 13 as illustrated in FIG. 3.

The method may also generally involves taking a measurement of optical plethysmography and brachial pressure, for example, to calculate the optical plethysmography index, and assessing capillary vitality by comparing all the foregoing measurements with normal values. This may also be done automatically as depicted in FIG. 4.

Figure 4:
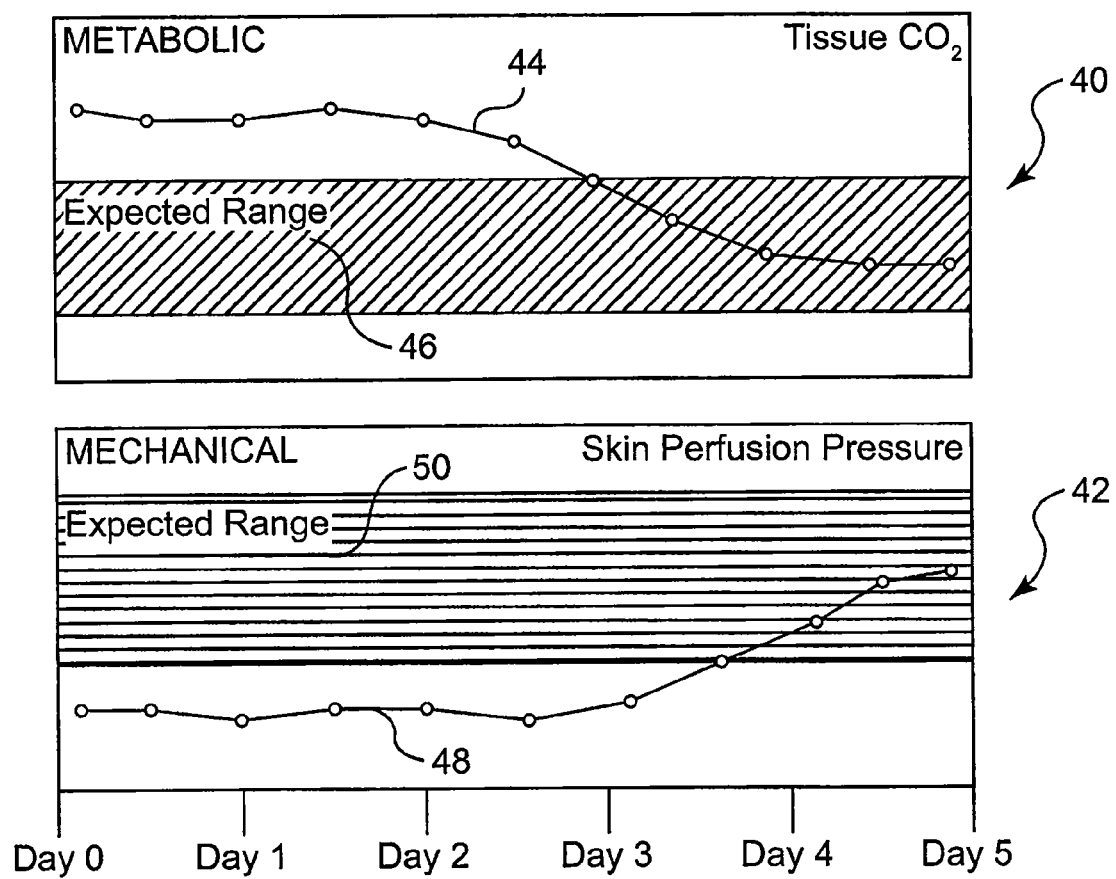
FIG. 4 is a schematic representation of a print out from the display of the present invention providing both metabolic and mechanical parameter output for assessing and monitoring capillary vitality.

FIG. 4 illustrates one exemplary output displayed on display monitor 30 of capillary vitality monitoring system 10, and includes metabolic parameter output 40 and mechanical parameter output 42. Metabolic parameter output 40 is in the form of a graph illustrating a measured metabolic parameter over a period of time. Any one of the metabolic parameters previously described may be measured and graphically displayed on display 30. However, in the present embodiment illustrated in FIG. 4, the measured metabolic parameter is tissue CO2, and the monitoring period is about five days. Metabolic parameter output 40 includes curve 44, which represents measured tissue CO2 values throughout the five day monitoring period, and a shaded area 46, which represents an expected range of tissue CO2 values that is indicative of capillary vitality. As shown in FIG. 4, curve 44 crosses into the area 46 representing the expected range of tissue CO2 around day three of the five day monitoring period.

Mechanical parameter output 42 is also in the form of a graph illustrating a measured mechanical parameter over a period of time. In the present embodiment illustrated in FIG. 4, the measured mechanical parameter is skin perfusion pressure, and the monitoring period is also about five days. Mechanical parameter output 42 includes curve 48, which represents measured skin perfusion pressure values throughout the five day monitoring period, and a shaded area 50, which represents an expected range of skin perfusion pressure values that is indicative of capillary vitality. As shown in FIG. 4, curve 48 crosses into the area 50 representing the expected range of skin perfusion pressure values between days three and four of the five day monitoring period.

As one skilled in the art will appreciate, metabolic parameter output 40 and mechanical parameter output 42 of FIG. 4 may be used in combination to assess and monitor capillary vitality. This combination of measurements as a predictor of capillary vitality yields vastly improved results over the measurement of either metabolic factors or mechanical factors alone.

Figure 5A:
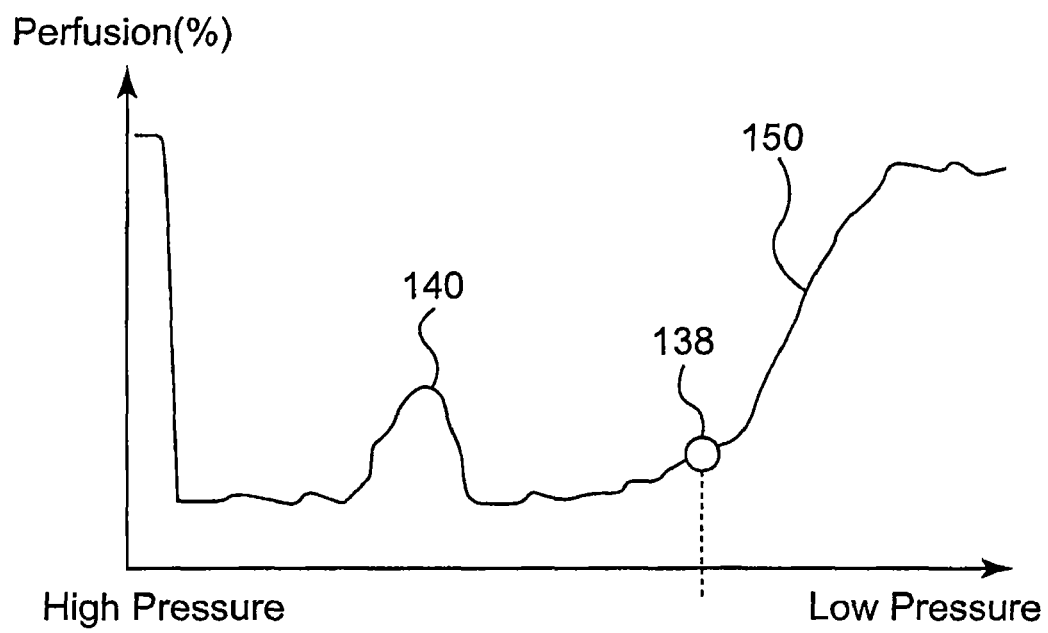
FIG. 5A is a schematic diagram illustrating the pressure line output display of the capillary vitality measurement system in accordance with the present invention with a spike indicating motion artifact.
Figure 5B:
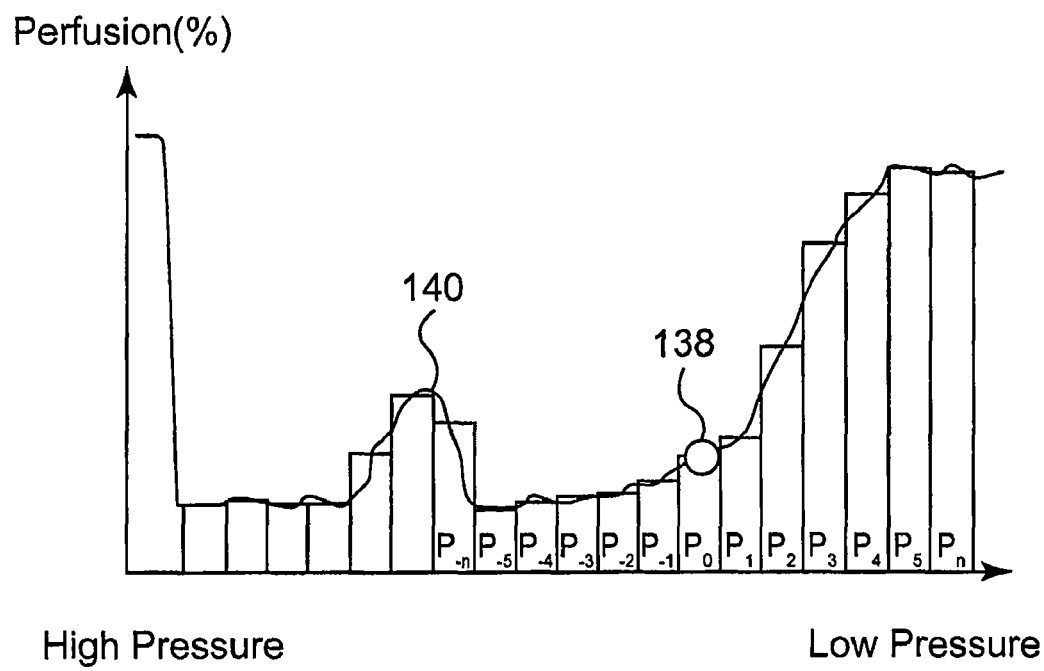
FIG. 5B is a schematic diagram illustrating the pressure line output display of the capillary vitality measurement system in accordance with the present invention with a spike indicating motion artifact, bars, and a true reading of surface perfusion pressure.

FIGS. 5A and B illustrate another exemplary output displayed on display monitor 30 of capillary vitality monitoring system 10. Optical probe 12 monitors microcirculatory flow within the observation volume of tissue 20. Microcirculation detected within the observation volume of tissue 20 may be expressed as a percent and displayed on the Y-axis of the perfusion pressure display instrument. As best seen in FIG. 5B, the percent value is shown as both a numeric value, typically from 0% to 10% and graphically is shown as a bar graph on the Y-axis of the instrument display 30. The capillary vitality monitoring system 10 also measures the pressure within the cuff 14 and displays the applied cuff pressure in millimeters of mercury on the X-axis of the display in descending uniform increments. As best seen in FIGS. 5A-B line 150 moves along the X-axis and shows the operator the cuff pressure that is currently being measured. FIG. 5A illustrates a pressure line that rises as pressure decreases and also displays motion artifact 140. Referring to FIG. 5B, the capillary vitality monitoring system in accordance with the present invention can also analyze numerous different criteria for detecting and rejecting motion artifact and in qualifying $P_0$ for a SPP value such as whether $P_0$ is within a valid range (i.e. from approximately 1 mmHg to approximately 150 mm Hg); whether the perfusion increase is large enough relative to a prior measurement (i.e. "step size"); whether flow is above a baseline value; whether the next steps following point $P_0$ are increasing or decreasing and the profile of perfusion change. If all criteria are met the skin perfusion pressure system will qualify $P_0$ as an SPP value. If $P_0$ has been qualified as an SPP value, a bar graph is overlaid on line 150, as best seen in FIG. 5B, and the SPP value 138 is recorded. As those skilled in the art can appreciate, any graphical representation can be used to depict the perfusion measurement data set.

In any case, one skilled in the art can appreciate that the display monitor 30 can illustrate these measurements as a numerical value or as bars. The foregoing measurements depicted in FIG. 4 can be superimposed over those of FIGS. 5A-B (or vice versa) and also can be superimposed over blood flow and pressure measurements to provide for superior diagnostic ability. If more than one wound is present and if this wound (s) is present in a separate angiosome, then these measurements will be repeated. The measured parameters for each angiosome wherein a wound is present will be comparatively aggregated to provide a Capillary Vitality Index (CVI). A schematic of sites of measurement will be displayed to provide automatic mapping of the CVI according to the number of sites measured and their anatomic location. One skilled in the art will appreciate that these combinations yield more than just predictable results.

The invention is useful in a variety of settings, such as in triage in emergency and disaster settings in which amputations and burn victims are prevalent, monitoring in anesthesia, intensive care, generally assess the ability of the wound or ulcer to heal, assessing the success of revascularization, and otherwise predict the behavior of healing such as with chronic, diseased wounds.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

What is claimed is:

1. A device for assessing capillary vitality comprising:
an inflatable cuff;
a blood flow sensor in communication with the cuff for measuring blood flow in a patient;
a pressure sensor in communication with the cuff for reading pressure levels in the cuff;
a pressure instrument in fluid communication with the cuff for inflation and deflation thereof, the pressure instrument comprising:
a source of pressurized air; and
a conduit connected to the source of pressurized air and the cuff, thereby placing the source of pressurized air in fluid communication with the cuff;
at least one metabolic sensor for measuring at least one metabolic condition of the patient;
a microprocessor operably coupled to said pressure instrument and capable of controlling pressurized airflow to and from the cuff, wherein said microprocessor is arranged to receive inputs from the blood flow, pressure and metabolic sensors;
a computer program executable by the microprocessor such that when executed, the computer program causes the microprocessor to:
initiate an automatic inflation sequence resulting in a no flow condition;
initiate an automatic deflation sequence;
automatically qualify a perfusion measurement as skin perfusion pressure value upon all conditions of a set of predetermined conditions being met during the deflation sequence;
initiate the measurement of at least one metabolic condition through said at least one metabolic sensor,
wherein a relationship among the measurements of blood flow, pressure and said at least one metabolic condition are displayed.

2. The device for assessing capillary vitality of claim 1 further comprising an array of metabolic sensors for measuring $pCO_2$, pH, NADH and $SaO_2$.

3. The device for assessing capillary vitality of claim 2 wherein said array of metabolic sensors are integrated into said cuff.

4. The device for assessing capillary vitality of claim 3 wherein said cuff is permeable.

5. A device for assessing capillary vitality comprising:
an inflatable cuff;
a blood flow sensor in communication with the cuff for measuring blood flow in a patient;
a pressure sensor in communication with the cuff for reading pressure levels in the cuff;
a pressure instrument in fluid communication with the cuff for inflation and deflation thereof, the pressure instrument comprising:
a source of pressurized air; and
a conduit connected to the source of pressurized air and the cuff, thereby placing the source of pressurized air in fluid communication with the cuff;
array of metabolic sensors for measuring $pCO_2$, pH, NADH and $SaO_2$ of the patient;
a microprocessor operably coupled to said pressure instrument and capable of controlling pressurized airflow to and from the cuff, wherein said microprocessor is arranged to receive inputs from the blood flow, pressure and metabolic sensors;
a computer program executable by the microprocessor such that when executed, the computer program causes the microprocessor to:
initiate an automatic inflation sequence resulting in a no flow condition;
initiate an automatic deflation sequence;
automatically qualify a perfusion measurement as a skin perfusion pressure value upon one or more conditions being met during the deflation sequence;
initiate the measurement of at least one metabolic factor through said at least one metabolic sensor,
wherein a relationship among the blood flow, pressure and metabolic measurements are displayed.

6. The device for assessing capillary vitality of claim 5 wherein said array of metabolic sensors are integrated into said cuff.

7. The device for assessing capillary vitality of claim 5 wherein said cuff is permeable.

* * * * *